United States Patent [19]
Wang et al.

[11] Patent Number: 5,441,516
[45] Date of Patent: Aug. 15, 1995

[54] TEMPORARY STENT

[75] Inventors: Lixiao Wang; Martin R. Willard, both of Maple Grove, Minn.; Thomas T. Tran, Coon Rapids, Minn.; Roger Hastings, Maple Grove, Minn.; Dale F. Schmaltz, Boulder, Colo.; Thomas J. Holman, Minneapolis, Minn.

[73] Assignee: Scimed Lifesystems Inc., Maple Grove, Minn.

[21] Appl. No.: 206,139

[22] Filed: Mar. 3, 1994

[51] Int. Cl.⁶ .......................................... A61M 29/00
[52] U.S. Cl. .................................. 606/198; 606/200; 604/104
[58] Field of Search ............... 606/191, 194, 195, 196, 606/197, 198, 200; 604/8, 53, 95-106; 128/898; 623/1, 12

[56] References Cited

U.S. PATENT DOCUMENTS

| | | | |
|---|---|---|---|
| 3,868,956 | 3/1975 | Alfidi et al. | |
| 3,993,078 | 11/1976 | Bergentz et al. | |
| 4,030,503 | 6/1977 | Clark, III | 606/159 |
| 4,130,904 | 12/1978 | Whalen | |
| 4,503,569 | 3/1985 | Dotter | |
| 4,512,338 | 4/1985 | Balko et al. | |
| 4,553,545 | 11/1985 | Maass et al. | |
| 4,820,298 | 4/1989 | Leveen et al. | 623/1 |
| 4,921,484 | 5/1990 | Hillstrad | 606/194 |
| 4,998,538 | 3/1991 | Delsanti | 128/898 |
| 5,002,560 | 3/1991 | Machold et al. | 606/198 |
| 5,034,001 | 7/1991 | Garrison et al. | 606/198 |
| 5,181,911 | 1/1993 | Shturman | 606/194 |
| 5,222,971 | 6/1993 | Willard et al. | 606/200 |

OTHER PUBLICATIONS

Transluminally-placed Coilspring Endarterial Tube Grafts Long-term Patency in Canine Popliteal Artery, Charles T. Dotter, MD., *Investigative Radiology*. Sep.-/Oct. 1969, No. 5, vol. 4, pp. 329-332.

Transluminal Expandable Nitinol Coil Stent Grafting: Preliminary Report[1], Dotter et al., *Radiology* 147, pp. 259-260, Apr. 1983.

Radiological Follow-up of Transluminally Inserted Vascular Endoprosthesis: An Experimental Study Using Expanding Spirals[1], D. Maass et al., *Radiology*, pp. 659-663 vol. 152, No. 3, Sep. 1984.

Nonsurgical Placement of Arterial Endoprostheses: A New Technique Using Nitinol Wire[1], Andrew Cragg, M.D., et al, *Radiology* vol. 147, pp. 261-263, Apr. 1983.

Improved Dilatation Catheter Balloons, Stanley B. Levy, Ph.D. *Journal of Clinical Engineering*, vol. 11, No. 4, Jul.-Aug. 1986.

*Primary Examiner*—Stephen C. Pellegrino
*Assistant Examiner*—William Lewis
*Attorney, Agent, or Firm*—Vidas, Arrett & Steinkraus

[57] ABSTRACT

Apparatus including a spiral coil body as a stent for temporarily supporting a body vessel internally, the spiral coil body being adjustable in diameter by relative rotation of at least one of the ends of the body from a proximal location.

32 Claims, 5 Drawing Sheets

TEMPORARY STENT

BACKGROUND OF THE INVENTION

This invention relates to stents which provide support to a vessel, such as a blood vessel, and in particular to stent apparatus that is temporary and removable.

Angioplasty and arthrectomy procedures are in some instances preferable to by-pass surgery. Although these procedures provide less traumatic alternatives to by-pass surgery, they are not without risk. It is possible that during or following such procedures, a vessel such as an artery or blood vessel may collapse or be susceptible to constriction or the formation of an internal "flaps". In some instances it may be necessary to abort or "bail-out" of the procedure due to complications.

In these situations it is necessary to maintain the integrity of the affected region of the vessel until it stabilizes or is repaired. That is, it may be necessary to provide support to the vessel on a temporary basis. To provide this support stents are used. Sometimes permanent stents are emplaced within the affected region of the vessel. Sometimes a temporary stent is emplaced and later removed.

In the case of the latter type, it is important that a temporary stent be easy to both install and remove. It is important that the stent not interfere with the flow of blood while it is in place. Due to branching in vessels such as blood vessels, it is important that the stent provide a blood flow path radially as well as axially or longitudinally.

It is also desirable to have the ability to deliver medicines and the like by infusion while the stent is in place.

Also, means for heating the stent to an elevated temperature at least during the initial contact between the stent and the interior wall of the vessel is sometimes desirable.

Accordingly, it is an object of this invention to provide an improved temporary stent apparatus with various such features which may be placed temporarily in a body, such as in a vascular system, and which may be readily removed at a later time.

SUMMARY OF THE INVENTION

This is accomplished by providing an improved stem apparatus which is readily adjustable in diameter size and length for insertion, emplacement and removal and which allows for perfusion, infusion and heating.

The improved apparatus takes the form of a catheter comprised of an elongate flexible shaft portion carrying a spiral coil body at its distal end portion. The shaft portion includes an inner tubular member attached to the distal end of the coil body and a concentrically surrounding outer tubular member attached to the proximal end portion of the coil body. Rotation of one tubular member relative to the other decreases the diameter of the coil body or increases its diameter, depending on the direction of rotation. Longitudinal movement of one tubular member relative to the other increases or decreases the length of the coil body.

Due to the coil configuration, the stent portion is readily perfusable and also allows radial as well as axial circulation. Infusion is readily accomplished through one of the tubular members. It is also readily heatable in a variety of ways as will be described hereinbelow.

With such as arrangement, the coil body may be wound down tightly in size for introduction and expanded to a larger diameter in size for emplacement as desired to support the vessel. The entire catheter structure may be left in place temporarily in the expanded condition. When removal is desired, the coil body is again wound down tightly from the proximal end of the catheter and the entire apparatus is removed by simply pulling it out.

As an alternative "fail safe" design, the coil body may be initially formed in a narrow diameter size equivalent to the constricted or "wound down" configuration as its normal state. To expand it, it is simply "wound up" and held up as long as desired. Upon release, it automatically "winds down" i.e., returns to its normal state due to the spring-like nature of the coil body.

In preferred arrangements the shaft portion of the catheter is constructed and arranged according to the invention so as to provide minimal torque absorption or loss to the tubular members of the shaft portions of the catheter desiring winding up or winding down of the stent coil body. This is important because it is desirable that, where rotational force is applied to the tubular member(s) at the proximal end of the catheter, the resultant torque reaches the stem spiral coil body with minimal loss in being transmitted through the shaft portion of the catheter.

DESCRIPTION OF PREFERRED EMBODIMENTS

In connection with the following description, it is assumed that the apparatus according to the invention is utilized in connection with a blood vessel containing a defect location or the like. However, the apparatus according to the present invention may be used also in other bodily environments involving other types of vessels or passageways wherein temporary stenting may be advantageous.

In use, the catheter apparatus as is already established in the art, can be inserted into a vessel or the like at an easily accessible location with the stent portion thereof maintained in a contracted state and moved through the vessel to the defect location or the like at which time the stent is expanded until it supports the vessel interiorly. The catheter is allowed to remain in place until such time as it is desired to remove it at which time the stent is again contracted and the catheter is pulled from the vessel.

Figures 1, 5:
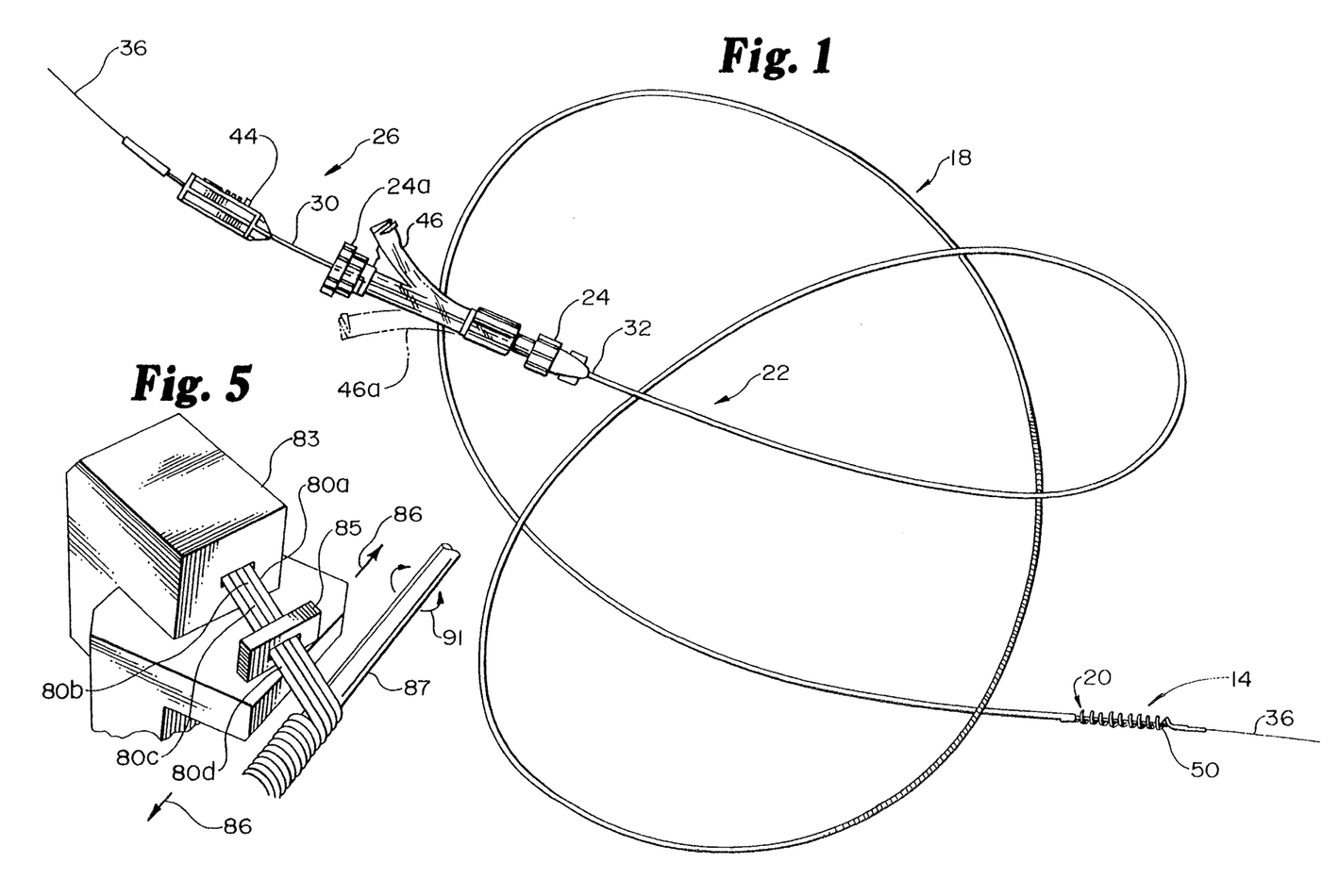
FIG. 1 depicts a first preferred embodiment of the present invention with the stent portion in a "relaxed" configuration.
FIG. 5 is a schematic of a wire winding apparatus for the inner and outer tubular means.

Referring to FIG. 1, a first embodiment of the invention is shown in overall view. The embodiment of FIG. 1 is a temporary stent catheter which can be placed in the vascular system or the like of a patient. Although the temporary stent catheter is particularly useful in procedures involving blood vessels, it may be used in other fluid carrying vessels in a patient's body. As used herein, the term "vascular system" refers to a vessel for conveying bodily fluids and other such passageways within the body. The temporary stent catheter is intended for placement in a vascular system for limited durations of time.

In the embodiment of the invention depicted in FIG. 1, the temporary stent catheter includes a perfusable stent portion generally indicated at 14 and a flexible shaft portion generally indicated at 18. Stent portion 14 is connected to a distal end portion generally indicated at 20 of shaft portion 18. When the temporary stent catheter is being used in the body of a patient, shaft portion 18 extends proximally from its connection to stent portion 14 through the vascular system and out of the body of the patient. The proximal end generally indicated at 22 of shaft portion 18 which extends out of the body of the patient is connected to a manifold 24.

Stent portion 14 is contractible and expandable so that it can be positioned in the vascular system at a specific location where needed in a contracted condition and then expanded to an appropriate size for supporting the vascular region interiorly. When in its expanded configuration, stent portion 14 provides support to the vascular walls thereby preventing constriction and maintaining the vascular lumen open.

Expansion and contraction of stent portion 14 inside the patient's body is accomplished from outside the patient's body by means of rotational manipulation of an actuator portion generally indicated at 26 from the proximal end 22 thereof which is located outside the patient's body. By operation through a pair of coaxial tubular members (best seen in FIG. 2) in shaft portion 18, the stent portion 14 which is in the form of a spiral coil body 50 may be expanded (wound-up) or contracted (wound-down) by relative axial rotation between the two tubular members, the opposite end portions of the coil body being attached to one of the tubular members, respectively. The change in diameter of the coil body occurs where the ends of the body are rotated relative to each other about the longitudinal axis of the coil.

Figures 2, 2A, 3:
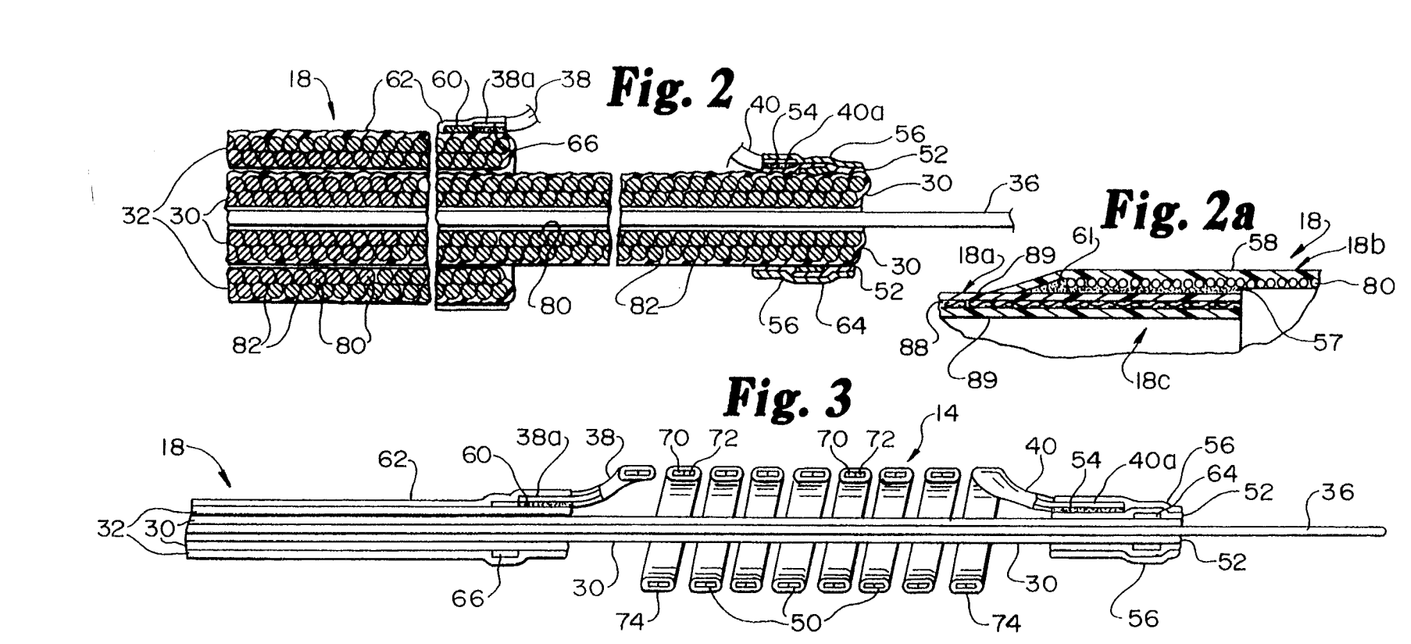
FIG. 2 is an enlarged longitudinal sectional view showing portions of the embodiment of FIG. 1 with parts cut away.
FIG. 2a is a longitudinal sectional view of another embodiment of the shaft portions of the catheter.
FIG. 3 is a simplified longitudinal cross-sectional view, with no hatching lines and part cut away, of a distal portion of the embodiment of FIG. 1 in enlarged view.

A more detailed showing of the construction and arrangement of one embodiment of shaft portion 18 is shown in FIG. 2 to which reference is now made in conjunction with continuing reference to FIG. 1. As can be seen in FIG. 2, shaft portion 18 is actually comprised of two coaxial flexible elongate tubular members generally indicated at 30 and 32 that connect to stent portion 14 as will be described further hereinbelow. Tubular member 32 is a concentrically surrounding outer tubular member with respect to inner tubular member 30. The tubular members 30 and 32 are constructed and arranged so as to allow relative longitudinal movement therebetween to thereby effect relative longitudinal movement of the ends 38 and 40 of coil body 50 so as to increase or decrease its length and diameter. Inner tubular member 30 accommodates a guide wire 36 in the manner known in the catheter art.

In this arrangement, outer tubular member 32 connects to a proximal end 38 of stent portion 14 and inner tubular member 30 connects to the distal end 40 of stent portion 14. Relative axial rotation of the tubular members 30 and 32 causes expansion and contraction of stem portion 14 as is explained in more detail below. By relative axial rotation, what is meant is that either tubular member alone may be individually rotated or both may be rotated simultaneously in opposite directions to effect a diameter change in stent 14. The distal end 20 of flexible shaft portion 18 remains in place in the body during the period of time that stent portion 14 is in place in the vascular system and during this time proximal end 22 of shaft portion 18 extends out of the patient's body. At the proximal end of shaft portion 18, the outer tubular member 32 terminates at manifold 24 or the like and the inner tubular member 30 terminates at a mechanical fitting or gripping means 44 or the like. With such an arrangement, by holding proximal end 24a of manifold 24 and twisting griping means 44, relative axial rotation as between inner tubular member 30 and outer tubular member 32 may be effected, which rotation is passed to stent portion 14 through connecting ends 38 and 40 as is described further hereinbelow.

In one embodiment, manifold 24 includes an infusion port 46 for administering fluids such as medicines and the like through the manifold and through the inner or outer tubular member 30 or 32, respectively, the route provided by the space between the two members being preferred i.e., passing fluid through the interior of tubular member 32 over the exterior of inner member 30. An additional port 46a is shown in phantom as being optional by means of which electrical leads may be introduced into the tubular member 30 for example or for introducing other elements and the like into various areas in the shaft 18.

The spiral coil configuration of stent portion 14 provides for an elongated expandable hollow tube-like stent 50 which can increase and decrease in diameter when the ends of the spiral coil 38 and 40 are subjected to axial rotational movement effected by the relative axial rotation of inner tube 30 and outer tube 32 as previously described. Its length can be increased and decreased by longitudinal movement of its ends. This also effects a change in diameter. Spiral coil 50 when subjected to such axial rotation of its ends about the longitudinal axis of the coil, will increase in diameter, or decrease in diameter, depending on the rotational direction thereof. For example, a decrease in diameter is shown in FIG. 4 in which the stent 14 is constricted for insertion whereas in FIG. 3, the stent is enlarged somewhat, although it can be enlarged even further with additional axial rotation.

Figure 4:
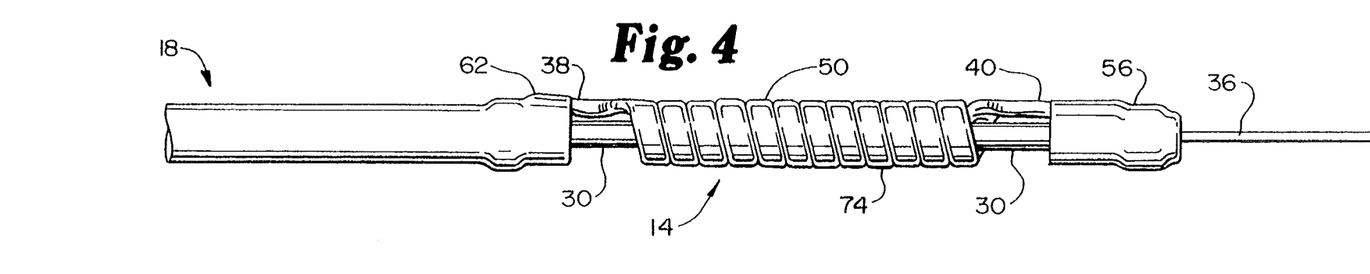
FIG. 4 is a longitudinal view of a portion similar to that of FIG. 3 showing the stent portion in a reduced contracted configuration.

As already indicated in a preferred "fail-safe" embodiment, the spiral coil body may be initially formed in a "wound down" configuration or constricted configuration as a normal state similar in size to that shown in FIG. 4. When being emplaced, it would be "wound-up" against its natural spring-like tendency to remain constricted. If not held up after being expanded, it would spring back or resume its small diameter automatically.

On the other hand, the spiral coil body may be formed such that its normal or relaxed state is larger in diameter similar to that shown in FIG. 1. In such an instance, the coil body is "wound down" to a constricted size in diameter during emplacement. Upon release, it self-expands to the relaxed condition and may be further "wound-up" to larger diameters as needed or desired.

The spiral coil body 50 of stent portion 14 may be provided in a wide range of sizes and stiffnesses to meet the requirements for use with different bodily situations in a patient's vascular system. It is constructed to be flexible enough to traverse its way to the region of the vascular system where it is to be located and expanded to provide support for that region of the vascular system while it is also constructed to provide the necessary support. Preferred materials are spring-like metal or plastic.

In one preferred embodiment, stent portion 14 is comprised of a spiral coil body of metal, a nitinol alloy being especially preferred. Nitinol is an alloy of nickel and titanium. A variety of proportions can be used in the alloy. Other metals, of course, may also be used as well as spring-like plastics.

Spiral coil body 50 of stent portion 14 terminates in a distal end 40 as shown in FIG. 2. Spiral coil body 50 per se is not shown in FIG. 2, being cut away for simplicity. It can however be seen in FIGS. 3 and 4 for example that inner tubular member 30 extends beyond the distal end of outer tubular member 32 and through the hollow tubular space of spiral coil body 50 to be connected to coil end 40 at the distal end of the catheter. Preferably, this connection is made by providing a section of heat shrink tubing 52 (shown in FIGS. 2 & 3) over the distal end of inner tubular member 30. The end 40(a) of end portion 40 of coil 50 is then secured to the heat shrink tubing 52 by means of an adhesive 54, preferably a cyanoacrylate adhesive. The end portion is then covered with a second band of heat shrink tubing 56 as shown in FIGS. 2 and 3.

The proximal end 38 of stent portion 14 is similarly secured to the distal end of outer tubular member 32 as seen in FIGS. 2 and 3. Outer tubular member 32 is preferably covered over its length with a layer or coating of polymeric material such as polytetrafluroethylene, a spot of cyanoacrylate adhesive 60 is then preferably applied and end 38(a) of end portion 38 is seated in the adhesive and then covered by an outer band of heat shrink tubing 62 which may also extend proximally over the entire shaft portion 18 if desired as is shown in FIG. 4, for example.

In order to provide a means by which the position of stent portion 14 in the body of a patient can be determined, one or more radial opaque markers such as 64 and 66 may be located to either end of stent portion 14 as shown in the Figures. These markers may be bands of radial opaque material such as platinum, tantalum, gold, tungsten or a tungsten-iridium alloy, for example which are merely crimped into position as shown.

In FIG. 3, the spiral coil body 50 of stent portion 14 is depicted in one preferred form made up of a plurality of parallel wound flat wire members or filars 70 and 72, two being shown although four or more may be used as desired. Filar members 70 and 72 as shown may preferably take the form of a somewhat flat rectangular in cross-section member, typically the rectangular cross-section might be 0.006"×0.003" in size for example and are coated with a polymeric coating such as a polyurethane 74. The edges formed on the flat wire are rounded off. A preferred method is used to radius the corners of the flat wire's electropolishing which removes edges or protrusions of the material and passivates the material without altering the bulk properties of the metals. For example, an embodiment utilizing Nitinol may comprise four ribbon wires wrapped adjacent each other and heat treated in the "up" state. Also, as can be seen in comparing FIG. 3 with FIG. 4, spiral coil body 50 is in a somewhat expanded condition in FIG. 3 as compared to a constricted or "wound-down" configuration in FIG. 4. These conditions can be maintained by merely holding the catheter at its proximal end out of the body portion by means of the gripping means 44 and manifold 24, or these end portions may be held in place by a suitable clamping arrangement or similar device which can be selectively disengaged as desired to permit reducing the diameter or enlarging the diameter of the spiral coil body 50. Also, the relaxed or normal condition can be built in the coil body to be of small diameter or any predetermined diameter, as already noted. Since inner tubular member 30 and outer tubular member 32 are longitudinally movable with respect to each other, it follows that spiral coil body 50 as it is wound and unwound will be free to decrease or increase in longitudinal length, as desired.

As has already been pointed out, an important feature of a preferred embodiment of this invention is the provision of minimal torque absorbing properties with respect to the inner and outer tubular members 30 and 32 so as to allow for minimal loss of torque when spiral coil body 50 of stent portion 14 is being wound up or wound down. Referring again to FIG. 2, this may be provided by one arrangement in which both inner tubular member 30 and outer tubular member 32 are comprised of a pair of oppositely wound helices of for example stainless steel windings. The inner helix 80 of inner tubular member 30 is formed by wires wound opposite to the direction of the outer helix 82 of tubular member 30. The pitch of the windings may be adjusted as desired to control longitudinal strengths and torque transmitting capability of the tubular member. Likewise, outer tubular member 32 is comprised of an inner helix winding 80 and an outer helix winding 82. Another embodiment of the inner and outer tubular members may comprise only a single layer wound helix. Such a shaft portion is described in two commonly assigned patent applications, Serial No. 08/205,245 and Serial No. 08/206,053, filed Mar. 3, 1994, of even date herewith, both entitled EX- PANDABLE INTERVASCULAR OCCLUSION MATERIAL REMOVAL DEVICES AND METHODS OF USE, the inventors being Hans A. Mische, Thomas V. Ressenmann, Anthony Urba and Steven Hackett. The entire content of these applications is incorporated herein by reference.

With respect to the stainless steel windings 80 and 82, an embodiment is provided in which four or more wires are wound in parallel in either a single or double layer. In such an instance, such a winding is referred to a four filar double layer or single layer, respectively. Such a winding may be accomplished as shown in FIG. 5 wherein four or more parallel wires 80a, 80b, 80c and 80d are held under tension in a wire supply means 83 and fed through a four wire slot 85 sized to hold four wires tightly together and parallel. These members are constructed and arranged to move longitudinally along a mandrel 87 as indicated by the arrows 86 while the mandrel is rotated as indicated by arrow to wind the wires over its length. One pass provides a four filar single layer tubular helically wound member. A reverse in direction and second pass provides a four filar double layer tubular helically wound member in which the helices of the two layers are disposed in opposite relationship.

The windings may extend over the entire length of flexible shaft portion 18 for both tubular members as shown in FIG. 2 or alternatively, to even further minimize the torque absorbing capabilities, a different type of shaft construction may be substituted at the proximal end portion of shaft 18 with respect to either of the tubular members 30 and 32 or both. For example, in the embodiment as shown in FIG. 2a, it has been found that the non-torque absorbing characteristics can be further improved by providing a polyimide composite with stainless steel braided tube as a proximal portion of outer tubular member 32 which is joined to a distal shaft portion of stainless steel winding like that shown in FIG. 2. For example, this distal portion may be only 15 inches in length. Likewise such a hybrid tubular member can be provided for inner tubular member 30 as well. As seen in FIG. 2a, such an arrangement may be accomplished by providing a proximal portion 18a of polyimide composite construction joined to a distal portion 18b with an area generally indicated at 18c of overlap. In the composite a polymer, specifically polyimide, conformingly encases a braided tube of stainless steel ribbon.

More specifically, the distal portion 18b may be of the construction shown in FIG. 2. The composite polyimide proximal portion 18a may be of COBRAID TM braided polyimide composite construction comprised of polyimide-encased braided flat stainless steel filament 0.0007 inches by 0.005 inches in cross-section if used as outer tubular member 32 and 0.0007 inches by 0.003 inches if used as inner tubular member 30. Individual strands of stainless steel ribbon are interwoven as shown in FIG. 2a to form a tubular braid 88. Polyimide material 89 encases the tubular braid on both the inner and outer surfaces of it. The polyimide material is thick enough to provide structured integrity to the tubular member and to render it fluid tight. On the other hand, it is thin enough to conform generally to the outer surface of braid. The polyimide may be for example Du-Pont Pyre-ML No. 5019. The braid may for example consist of 16 ribbons of stainless steel, such as 304 springtemper. Typically, for outer member 32 the OD will preferably be 0.042 inches and the ID will be 0.035 inches. For inner member 30 the OD will be 0.033 inches and the ID will be 0.026 inches. In overlap area 18c, an adhesive such as a 2-part urethane adhesive 57 such as 3M #3549 may be inserted between the wire winding 59 and the polyimide braided tubing 18a. The proximal joint may be filled with another 2-part urethane adhesive 61 such as H.B. Fuller #3507 to smooth the outer surface. Finally, over the overlap area and the distal portion 18b, a polytetrafluoroethylene coating 58 may be applied.

A braided embodiment for the proximal portion of either tubular member 30 or 32 is also shown in detail in U. S. patent application Ser. No. 07/867,164, filed Apr. 9, 1962 which is commonly assigned. It is incorporated in its entirety herein by reference.

Another hybrid embodiment of a shaft tubular member may comprise a stainless steel hypotube be substituted for the distal winding portion. A hypotube is merely an elongate, thin wall, flexible robe of small size such as 0.028 inch ID and 0.032 inch OD.

Figures 6, 6A, 7, 8, 9:
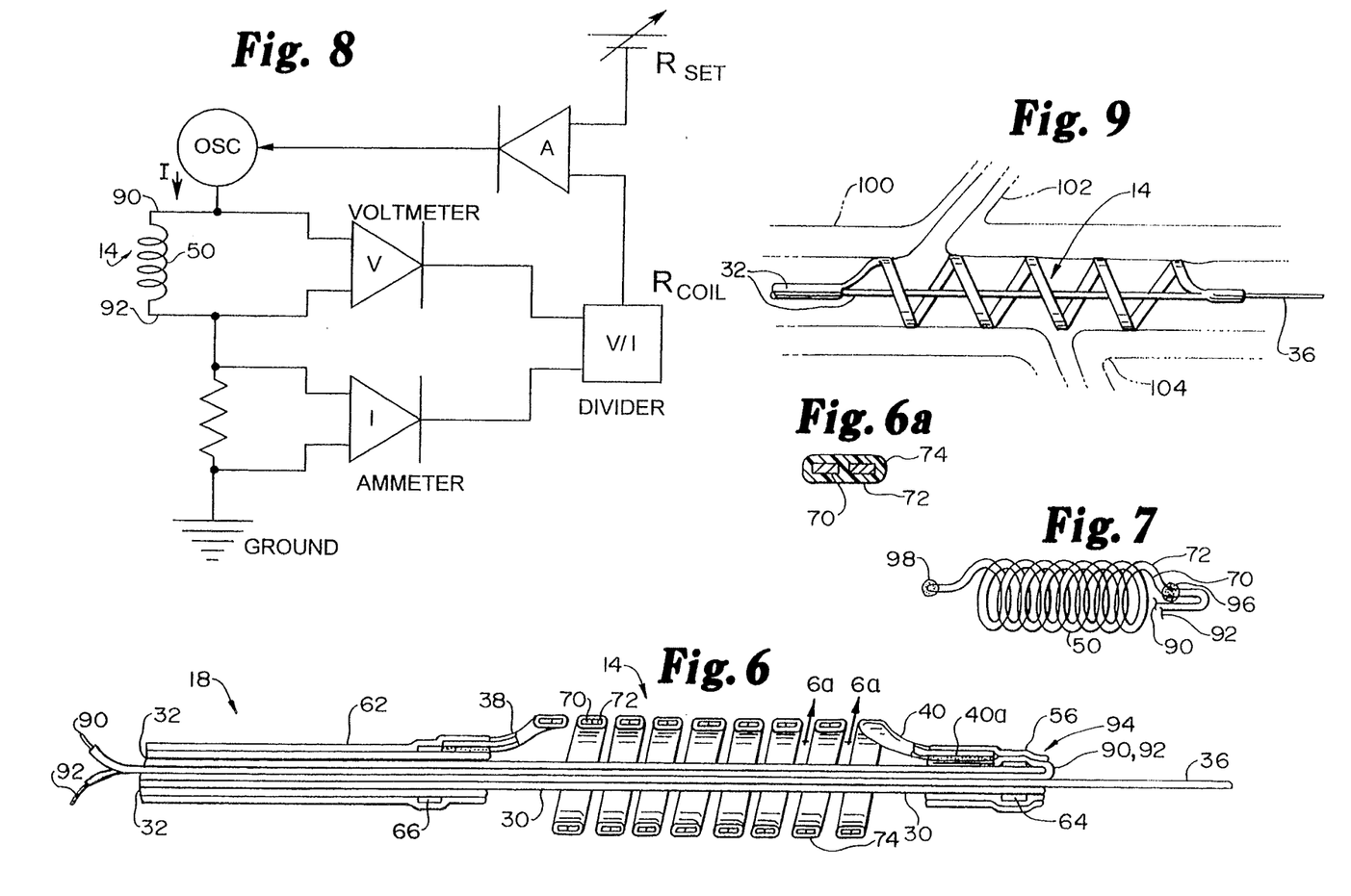
FIG. 6 is a longitudinal sectional view similar to that of FIG. 3 showing an embodiment of the apparatus including means for electrically heating the stent portion thereof.
FIG. 6(a) is a cross-section through lines 6a—6a of FIG. 6 showing the insulated arrangement of the two parallel wires in the stent core body.
FIG. 7 is a schematic showing the path of the electrical conductors in the stent coil body.
FIG. 8 is an electrical schematic showing electrical supply arrangement for providing electrical energy to heat the stent portion of the embodiment of FIG. 6.
FIG. 9 is a schematic showing of the stent portion of the apparatus in an expanded condition schematically showing the ability of the stent to allow for perfusion and infusion and radial flow even in branching situations in a body vessel.

Referring now to FIGS. 6, 7, and 8, an exemplary alternative embodiment of the invention will be described in which an electrical means for heating the spiral coil body 50 or stent portion 14 is disclosed and described. As can be seen in FIG. 6, a pair of electrical leads 90 and 92 extends through inner tubular member 30 from the proximal end of the catheter in a distal direction all the way to the distal end where they connect to the metal wires 70 and 72 of spiral coil body 50 as shown generally at 94. This is best seen schematically in FIG. 7 which shows leads 90 and 92 being connected to wires 70 and 72, respectively, by means of an insulative patch of adhesive such as a cyanoacrylate 96 and at the proximal end 98 (FIG. 7) of spiral coil 50 wires 70 and 72 are connected so as to form a continuous path which extends through lead 90 from a connecting electrical source (to be described below) into wire 70 and then in a return path to wire 72 back through wire lead 92 to the electrical source. Wires 70 and 72 are interconnected at 98 by means of a solder spot or the like. As can be seen in FIG. 6(a), which is a cross-section of one coil portion of spiral 50, wires 70 and 72 are separated and insulated from each other by means of coating 74 to establish the desired electrical path.

An example of one suitable electrical source means is shown in FIG. 8 which is attached to leads 90 and 92 and which provides electrical energy to cause a heating of wires 70 and 72 to an elevated temperature. When it is desired to raise the temperature of the stent coil 50 to a set value, Tset, and control the stent coil 50 temperature at Tset, operation of the circuit in FIG. 8 is as follows. Heating of the stent 14 is accomplished by passing A.C. current through the stent coil 50. The frequency of the A.C. current is selected to be above about 100,000 cycles/second because the body's nervous and muscular systems do not react to these high frequencies.

The stent coil 50 temperature is measured by measuring the resistance of the stent coil. The stent coil 50 resistance increases monotonically with temperature, so that a set resistance Rset, corresponds to only one set temperature, Tset.

The stent coil 50 temperature is controlled by controlling the amplitude of the A.C. current through the coil in proportion to the difference between the set coil resistance and the measured coil resistance. Thus, when the coil resistance is less than the set value (Rcoil<Rset or Tcoil<Tset), the coil heating current is driven to a higher value. Conversely, when the coil resistance is larger than the set value (Rcoil>Rset or Tcoil>Tset), the coil hearing current is driven to a lower value. In this way, the coil temperature is automatically controlled at the set value.

The amplitude controlled oscillator (OSC) drives current through the stent coil 50 and a sampling resistor to ground. The voltage across coil 50 is measured and the current through the coil is also measured by measuring the voltage across the sampling resistor. The measured voltage is divided by the measured current (V/I) to determine the coil resistance by means of a V/I divider. The coil 50 resistance is subtracted from a set resistance (Rset) and this difference controls the amplitude of the oscillator current.

Thus, when D.C. power is supplied to the voltmeter, the ammeter, the amplifier and the oscillator, the oscillator current is at its maximum value. When Rcoil (or Tcoil) approaches Rset (Tset) the oscillator current is controlled in proportion to Rset-Rcoil (Tset - Tcoil) to maintain the coil 50 temperature at the set value. The schematic of FIG. 8 can be implemented via analog circuitry as indicated, or via a digital computer or microprocessor which implements these functions digitally in known manner. More detailed information concerning such an electrical arrangement is found in co-pending application Ser. No. 08/055,702; filed Apr. 28, 1993; entitled "Apparatus And Method for Performing Diagnostics and Intravascular Therapies, which is assigned to the same assignee as is this invention and incorporated herein by reference.

In FIG. 9, the spiral coil configuration of stent portion 14 is shown in a supporting relationship with a vessel 100 which contains branching portions 102 and 104. It can readily be seen that the configuration of the spiral coil readily allows not only for longitudinally flow-through of fluid in the vessel, but also for perfusion and radial flow into the side branches.

Figure 10:
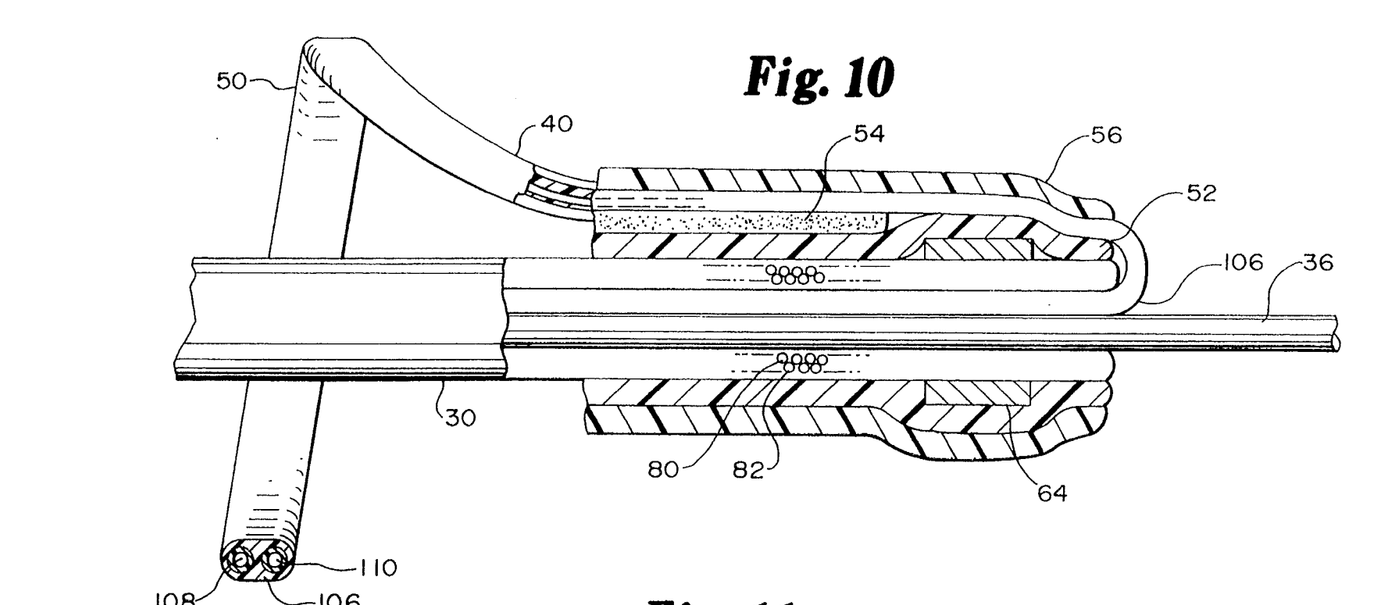
FIG. 10 is a longitudinal, cross-sectional view of a distal portion of an apparatus according to the invention wherein an alternate arrangement for heating the stent coil body is utilized, the stent coil body consisting of a hollow polymeric material with a pair of lumens for accommodating flow of a heating fluid.

Referring now to FIG. 10, an alternative means for heating a spiral coil configured stent portion 14 is shown in which the spiral coil 50 is comprised of a polymeric material 106 such as polyethylene containing two lumens 108 an 110 by means of which fluid may flow through the spiral coil body 50. Circulation is provided by using lumen 108 for input and lumen 110 for outlet. When the fluid is heated, such as a heated saline solution at about 60° C., and introduced into member 106 at the proximal end of the catheter in the known fashion, member 106 extending through tubular member 30 as shown, an elevated temperature is provided in the coil body 50. The fact that end 40 of member 106 is formed into a spiral coil configuration is indicated partially at 50.

Figure 11:
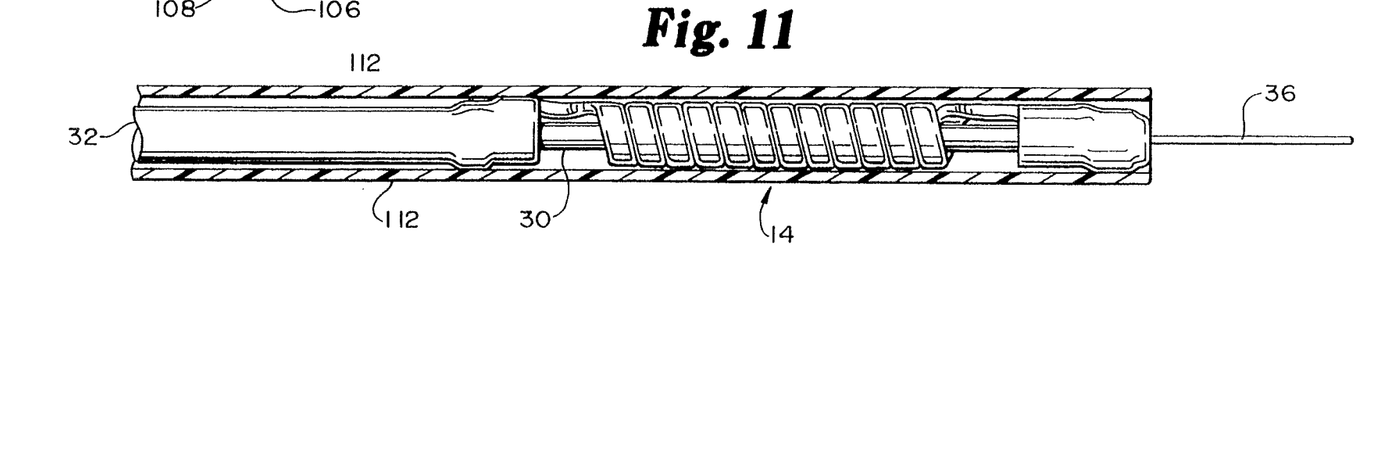
FIG. 11 is a showing of a catheter stent including a covering/retractable sheath.

As shown in FIG. 11, the catheter stent may be provided with a flexible covering sleeve or sheath 112. Sheath 112 may be a polymeric tube such as polytetrafluroethylene or other fluropolymer or polyethylene, for example and may extend over a substantial length of the catheter stent so as to cover the stent portion 14 as shown in the Figure and so as to present a proximal end (as at portion 22 in Fig. 1) within reach of the surgeon once the stent is in place in the patient's body. In reality, any material which provides a flexible tube or sleeve may be used as the sheath. The surgeon may simply grasp the proximal end of sheath 112 and pull on it so it slides proximally on the catheter to uncover stent coil 50 in part or in toto as desired. This may be aided by including a lubricous material such as polyethylene oxide between the sheath and catheter. During placement, the surgeon may, for purposes of flexibility, uncover part or all of the coil.

When it is desired to withdraw the catheter stent and after it has been "wound down" or constricted by rotation, the surgeon may simply grasp sheath 112 and pull the catheter stent into it and then retract the entire apparatus. On the other hand, the coil may be stretched longitudinally first to elongate it and then wound as it is retracted into the sheath. Or, it may be elongated and simply pulled into the sheath.

Figures 12, 13, 14:
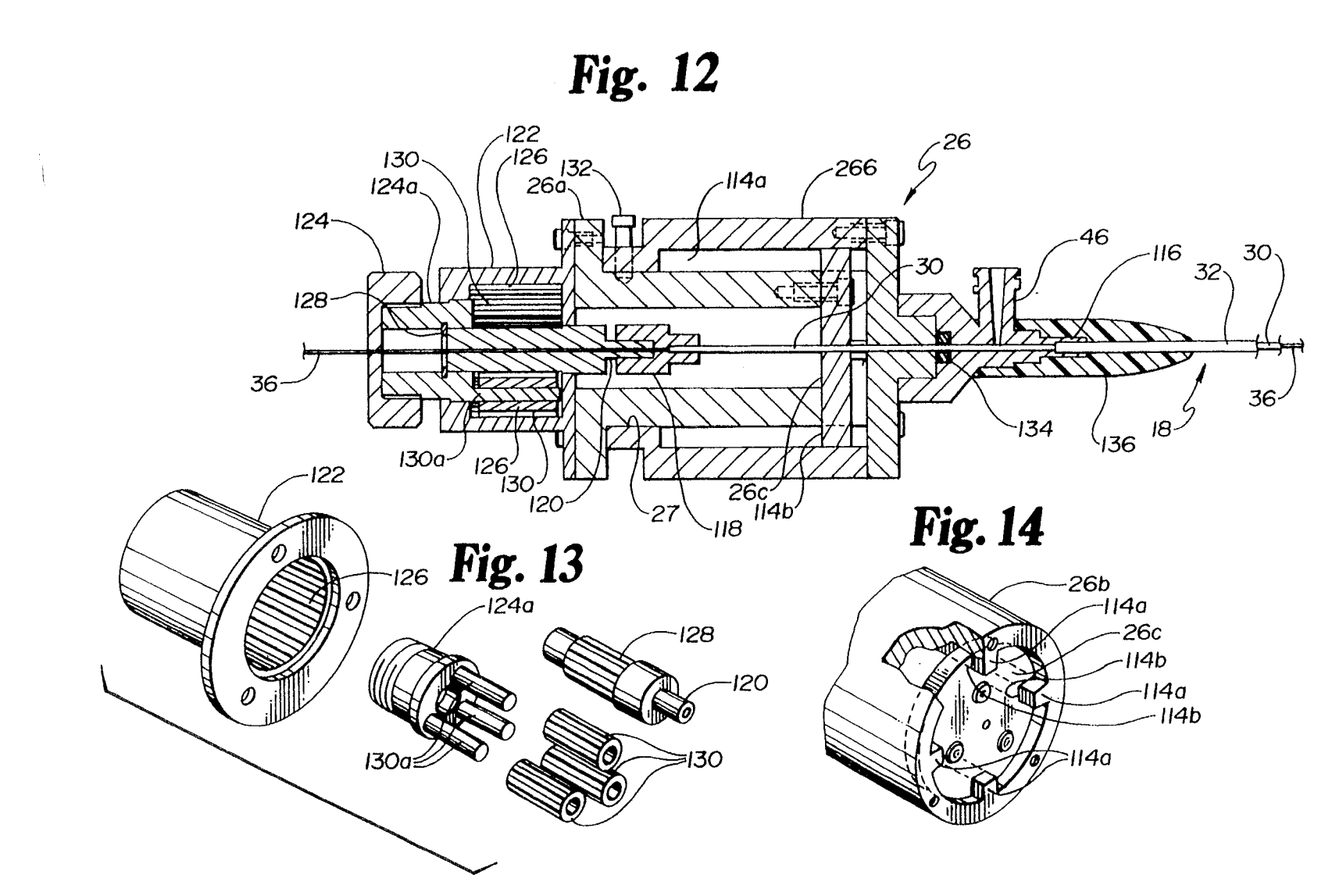
FIG. 12 shows an alternate manifold arrangement.
FIG. 13 is an exploded pictorial view of the gear arrangement in Figure 12.
FIG. 14 is a fragmentary pictorial view of the rib and groove arrangement in FIG. 12.

Referring to FIGS. 12, 13 and 14 an alternate manifold 26 arrangement is shown. This arrangement includes a two-piece manifold body of telescoping construction. Specifically, body portion 26a is slidably received within a bore 27 in body portion 26b to provide for longitudinal telescoping movement of inner tubular member 30 with respect to outer tubular member 32. A rib and groove arrangement 114a and 114b is included on body portions 26a and 26b to allow for longitudinal or axial movement but to prevent relative rotation of the body portions 26a and 26b. Specifically, for example, projecting ribs 114a may be integras with body portion 26b and mating grooves 114b may be formed in end body portion 26c which is slidably received in body portion 26b as the distal end of body portion 26a. This is best seen in FIG. 14.

The proximal end of outer tubular member 32 is fixedly connected to end portion 116 of body 26b. This portion may also include one or more infusion or inlet ports 46 in communication with the space between the inner tubular member 30 and the outer tubular member 32, as shown. Also, a port may communicate with the interior of inner tubular member 30 if desired. Inner tubular member 30 extends proximally beyond the proximal end of outer tubular member 32 and end portion 116 to the inside of portion 26a where it is connected to a device coupler 118 which is in turn connected to the output shaft 120 of gear housing 122. Gear housing 122 is fixedly connected to proximal end of body portion 26a. Housing 122 includes a turn knob 124 by means of which rotary motion can be input into housing 122 manually.

The gear arrangement inside housing 122 may be of the planetary type, although other type may be used. In the particular arrangement shown, the input shaft 124a of turn knob 124 is operatively connected to turn three planetary gears 130 which are positioned between a fixed peripheral input ring gear 126 and central output gear 128. Connection between input shaft 124a and the planetary gears is by means of three pins 130a which rotatably carry each of the planetary gears. Centered in the gear arrangement is the output gear 128 which is connected to output shaft 120 and coupler 118. This arrangement is best seen in FIG. 13.

Depending on the relative gear sizes, an operating ratio of 5:1 to 25:1 is readily available in a mechanical gear arrangement to provide higher output rotation turns than input rotation turns. The mechanical advantage is obtained as the planetary gears are rotated about the center gear and rotated on their axes within the fixed ring gear by turning the turn knob, the planetary gears driving the central gear at a mechanical advantage. The manifold housing and all parts may be made of plastic such as polycarbonate and the fixed ring gear 124 may be molded inside the gear housing member 122.

A lock screw 132 may be included to selectively lock body portions 26a and 26b together. Also, an O-ring seal 134 may be included to prevent back flow from port 46. Lastly, a strain relief body 136 of flexible plastic such as silicone rubber may be included as shown to prevent kinking of catheter shaft portion 18.

While this invention may be embodied in many different forms, there are described in detail herein specific preferred embodiments of the invention. This description is an exemplification of the principles of the invention and is not intended to limit the invention to the particular embodiments illustrated.

What is claimed is as follows:

1. Removable apparatus for temporarily supporting a region of a vessel in a body, the apparatus comprising a catheter having proximal and distal end portions, an elongate flexible shaft portion and a stent portion carried by a distal end portion of the shaft portion the shaft portion including an elongate inner tubular member having an exterior, and an elongate outer tubular member concentrically positioned around the exterior of the inner tubular member, each of said tubular members having a proximal end and a distal end, the tubular members being movable axially with respect to each other and the distal end of the inner tubular member extending distally beyond the distal end of the outer tubular member, wherein at least the distal elongate portions of the inner and outer tubular members are comprised of closely wound helices of metal wire;

the stent portion being comprised of a spring-like spiral coil body having proximal and distal end portions, the coil body being positioned with respect to the shaft portion of the catheter so that the distal end portion of the inner tubular member extends longitudinally through the coil body, the distal end portion of the coil being fixedly secured to the inner tubular member and the proximal end portion of the coil body being fixedly secured to the outer tubular member whereby axial rotation of at least one tubular member effects rotation of at least one of the ends of the coil body with respect to the other and, depending on the direction of the rotation, enlarges or decreases the diameter of the spiral coil body, and means at the proximal end portion of the catheter operatively connected to the shaft portion for effecting the axial rotation of the at least one tubular member and controlling same.

2. The apparatus of claim 1 including heating means associated with the catheter for heating the spiral coil body to an elevated temperature.

3. The apparatus of claim 1 wherein the spiral coil body is of plastic.

4. The apparatus of claim 1 wherein the spiral coil body is of metal.

5. The apparatus of claim 4 including electrical means associated with the catheter and in communication with the spiral coil body for heating the spiral coil body to an elevated temperature.

6. The apparatus of claim 5 wherein the electrical means passes AC current throught the coil at a frequency which does not affect the body.

7. The apparatus of claim 6 wherein the frequency of the AC current is above about 100,000 cycles per second.

8. The apparatus of claim 4 wherein the metal is a nitinol alloy.

9. The apparatus of claim 1 including a retractable polymeric sheath associated with the catheter and in communication with the stent portion for selectively covering and uncovering the stent portion.

10. The apparatus of claim 1 wherein the spiral coil body is comprised of at least one ribbon-like metal winding which is rectangular in cross-section.

11. The apparatus of claim 1 wherein the spiral coil winding is comprised of at least one metal winding including a polymeric coating thereon.

12. The apparatus of claim 1 including radiopaque marker means associated with the apparatus for identifying and locating the stent portion, said marker means being proximal to said stent portion.

13. The apparatus of claim 1 wherein the initial configuration of the spiral coil body is constricted for failsafe purposes, said apparatus being constructed and arranged to be held in an expanded state, and to automatically return to its constricted state upon release.

14. The apparatus of claim 1 wherein the closely wound helices each comprise a single layer.

15. The apparatus of claim 1 wherein the closely wound helices each comprises at least two oppositely wound windings forming multiple layers.

16. The apparatus of claim 1 wherein the closely wound helices are each of at least the two filar double layer type.

17. The apparatus of claim 16 wherein the closely wound helices are of at least the four filar double layer type.

18. The apparatus of claim 1 wherein a proximal elongate portion of the outer tubular member is comprised of a polymeric/braided composite joined to a distal wire wound portion.

19. The apparatus of claim 18 wherein the polymeric portion of the composite is polyimide.

20. The apparatus of claim 18 wherein the wire wound portion is of at least the four filar double layer type.

21. The apparatus of claim 1 wherein a proximal elongate portion of the inner tubular member is comprised of a polymeric/braided composite joined to a distal wire wound portion.

22. The apparatus of claim 21 wherein the polymeric portion of the composite is polyimide.

23. The apparatus of claim 21 wherein the wire wound portion is of at least the four filar double layer type.

24. The apparatus of claim 1 including means connected to the proximal end portion of the catheter for introducing infusion fluid through one of the tubular members.

25. The apparatus of claim 24 wherein the infusion fluid includes a medicament.

26. The apparatus of claim 1 wherein the axial movement of the inner and outer tubular members with respect to each other is effected by a two-piece telescoping arrangement, one piece being connected to the inner tubular member, the other piece being connected to the outer tubular member.

27. The apparatus of claim 1 wherein at least a portion of the length of either the inner or outer tubular member is comprised of a stainless steel hypotube.

28. The apparatus of claim 1 wherein the spiral coil body is comprised of a plurality of parallel wound members.

29. Removable apparatus for temporarily supporting a region of a vessel in a body, the apparatus comprising a catheter having proximal and distal end portions, an elongate flexible shaft portion and a stent portion carried by a distal end portion of the shaft portion;

the shaft portion including an elongate inner tubular member having an exterior and an elongate outer tubular member concentrically positioned around the exterior of the inner tubular member, each of said tubular members having a proximal end and a distal end, the tubular members being movable axially with respect to each other and the distal end of the inner tubular member extending distally beyond the distal end of the outer tubular member;

the stent portion being comprised of a spring-like spiral coil body, said coil body being further comprised of at least two parallel wound ribbons and having proximal and distal end portions, the coil body being positioned with respect to the shaft portion of the catheter so that the distal end portion of the inner tubular member extends longitudinally through the coil body, the distal end portion of the coil being fixedly secured to the inner tubular member and the proximal end portion of the coil body being fixedly secured to the outer tubular member whereby axial rotation of at least one tubular member effects rotation of at least one of the ends of the coil body with respect to the other and, depending on the direction of the rotation, enlarges or decreases the diameter of the spiral coil body, and means at the proximal end portion of the catheter operatively connected to the shaft portion for effecting the axial rotation of the at least one tubular member and controlling same.

30. Removable apparatus for temporarily supporting a region of a vessel in a body, the apparatus comprising a catheter having proximal and distal end portions, an elongate flexible shaft portion and a stent portion carried by a distal end portion of the shaft portion;

the shaft portion including an elongate inner tubular member having an exterior, an elongate outer tubular member concentrically positioned around the exterior of the inner tubular member, each of said tubular members having a proximal end and a distal end, said tubular members being movable axially with respect to each other, a two-piece telescoping arrangement for effecting said longitudinal relative movement between the inner and outer tubular members, one piece being connected to the inner tubular member, the other piece being connected to the outer tubular member, said telescoping arrangement further comprising means for preventing rotation of the two pieces relative to each other, the one piece being adapted to impart rotary turning motion to the inner tubular member, and the distal end of the inner tubular member extending distally beyond the distal end of the outer tubular member;

the stent portion being comprised of a spring-like spiral coil body having proximal and distal end portions, the coil body being positioned with respect to the shaft portion of the catheter so that the distal end portion of the inner tubular member extends longitudinally through the coil body, the distal end portion of the coil being fixedly secured to the inner tubular member and the proximal end portion of the coil body being fixedly secured to the outer tubular member whereby axial rotation of at least one tubular member effects rotation of at least one of the ends of the coil body with respect to the other and, depending on the direction of the rotation, enlarges or decreases the diameter of the spiral coil body, and means at the proximal end portion of the catheter operatively connected to the shaft portion for effecting the axial rotation of the at least one tubular member and controlling same.

31. The apparatus of claim 30 including mechanical means for increasing the ratio of the number of turns from input to output, the means being operatively associated/connected with the telescoping piece for effecting rotational input and output between it and the inner tubular member and imparting a mechanical advantage to the output.

32. The apparatus of claim 31 wherein the mechanical means includes a gear arrangement.

* * * * *

UNITED STATES PATENT AND TRADEMARK OFFICE
CERTIFICATE OF CORRECTION

PATENT NO. : 5,441,516
DATED : August 15, 1995
INVENTOR(S) : Wang, et al

It is certified that error appears in the above-indentified patent and that said Letters Patent is hereby corrected as shown below:

Column 1, line 45, delete "stem" and insert --stent--

Signed and Sealed this

Seventeenth Day of October, 1995

Attest:

BRUCE LEHMAN

Attesting Officer

*Commissioner of Patents and Trademarks*